(12) United States Patent
Kon et al.

(10) Patent No.: US 8,747,939 B2
(45) Date of Patent: *Jun. 10, 2014

(54) NUTRIENT COMPOSITION

(71) Applicant: Ajinomoto Co., Inc., Chuo-ku (JP)

(72) Inventors: Itaru Kon, Shizuoka (JP); Naoki Hayashi, Shizuoka (JP); Tatsuro Tanaka, Kawasaki (JP); Hisayuki Uneyama, Kawasaki (JP); Shinji Somekawa, Shizuoka (JP)

(73) Assignee: Ajinomoto Co., Inc., Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/869,120

(22) Filed: Apr. 24, 2013

(65) Prior Publication Data

US 2013/0243933 A1 Sep. 19, 2013

Related U.S. Application Data

(63) Continuation of application No. 12/038,290, filed on Feb. 27, 2008, which is a continuation of application No. PCT/JP2006/314192, filed on Jul. 18, 2006.

(30) Foreign Application Priority Data

Aug. 29, 2005 (JP) .................................. 2005-248187

(51) Int. Cl.
*A23J 1/00* (2006.01)

(52) U.S. Cl.
USPC ............. 426/656; 426/648; 426/590; 426/74; 426/73; 426/65; 127/43; 424/439

(58) Field of Classification Search
USPC ................. 426/656, 73, 74, 590, 65; 424/439
See application file for complete search history.

(56) References Cited

U.S. PATENT DOCUMENTS 4,213,896 A * 7/1980 Davis ............................ 530/360
4,695,463 A * 9/1987 Yang et al. .................... 424/440
(Continued)

FOREIGN PATENT DOCUMENTS

CN 1104890 A 7/1995
EP 0 914 779 A2 5/1999
(Continued)

OTHER PUBLICATIONS

Atsuko: JP 2004-097119 A; Feb. 4, 2004.*

(Continued)

*Primary Examiner* — Patricia George
(74) *Attorney, Agent, or Firm* — Oblon, Spivak, McClelland, Maier & Neustadt, L.L.P.

(57) ABSTRACT

The present invention relates to a nutrient composition which contains at least a carbohydrate, a lipid, a protein, and a mineral, and is liquid or semisolid, characterized in that the volume-based median size (d50) of particles in the nutrient composition is 5 to 100 μm and water-insoluble particles having a protein insolubilized by a divalent cation are contained as a major component of the nutrient composition, or a nutrient composition which contains at least a carbohydrate, a lipid, a protein, and a mineral, and is liquid or semisolid, characterized in that water-insoluble particles having a protein insolubilized by a divalent cation are contained as a major component of the nutrient composition and the mass of the protein with respect to the total moles of divalent ions forming the water-insoluble particles is 1.5 to 3 g/mmol.

6 Claims, 3 Drawing Sheets

(56) References Cited

U.S. PATENT DOCUMENTS

| | | | |
|---|---|---|---|
| 5,006,559 | A | 4/1991 | Askanazi et al. |
| 5,108,767 | A * | 4/1992 | Mulchandani et al. ......... 426/72 |
| 5,488,038 | A * | 1/1996 | Kondo et al. .................... 514/41 |
| 5,514,655 | A * | 5/1996 | DeWille et al. ................ 514/5.5 |
| 5,514,656 | A * | 5/1996 | Cope et al. ..................... 514/5.5 |
| 5,635,199 | A | 6/1997 | Trimbo et al. |
| 6,287,623 | B1 | 9/2001 | Nakayama et al. |
| 6,495,190 | B1 | 12/2002 | Yaginuma et al. |
| 6,531,448 | B1 * | 3/2003 | Brader ............................ 514/6.2 |
| 2003/0130217 | A1 * | 7/2003 | Raz et al. ......................... 514/44 |
| 2003/0138476 | A1 | 7/2003 | Van Leeuwen et al. |
| 2004/0096478 | A1 | 5/2004 | Whippie et al. |
| 2004/0197381 | A1 | 10/2004 | Kanie |
| 2004/0208955 | A1 | 10/2004 | Carr et al. |

FOREIGN PATENT DOCUMENTS

| | | |
|---|---|---|
| JP | 57-099158 | 6/1982 |
| JP | 01-199565 | 8/1989 |
| JP | 1-243970 | 9/1989 |
| JP | 06-141783 | 5/1994 |
| JP | 8-98647 | 4/1996 |
| JP | 11-009222 | 1/1999 |
| JP | 2000-77 | 1/2000 |
| JP | 2001-61444 | 3/2001 |
| JP | 2001-217531 | 8/2001 |
| JP | 2002-119246 | 4/2002 |
| JP | 2002-142720 | 5/2002 |
| JP | 2003-201230 | 7/2003 |
| JP | 2003-530411 | 10/2003 |
| JP | 2004-26844 | 1/2004 |
| JP | 2004-97119 | 4/2004 |
| JP | 2006-109723 | 4/2006 |
| JP | 2006-182767 | 7/2006 |
| RU | 2003 132 462 A | 2/2005 |
| WO | WO 02/098242 A1 | 12/2002 |

OTHER PUBLICATIONS

STIC Search results of Aug. 5, 2013.*
International Search Report issued on Sep. 12, 2006, in PCT/JP2006/314192 (with translation). References cited were filed on Apr. 24, 2013.
European Search Report issued on Jul. 27, 2009, in EP 06781205.7. References cited were filed on Apr. 24, 2013.
U.S. Office Action issued Nov. 30, 2009, in parent application U.S. Appl. No. 12/038,290. References cited were filed on Apr. 24, 2013.
Russian Decision on Grant issued on Jan. 11, 2010, for RU 2008107750 (with translation).
U.S. Office Action issued Jan. 18, 2011, in parent application U.S. Appl. No. 12/038,290. References cited were filed on Apr. 24, 2013.
U.S. Office Action issued Aug. 2, 2012, in parent application U.S. Appl. No. 12/038,290. References cited were filed on Apr. 24, 2013.
U.S. Office Action issued May 16, 2013, in parent application U.S. Appl. No. 12/038,290.
Medicine.net.com: Definition Enteral Nutrition: Nov. 5, 2004: http://web.archive.org/web/20041105102115/http://www.medterms.com/script/main/art.asp?articlekey=39500.
American Heritage@ Stedman's Medical Dictionary Copyright© 2002, 2001, 1995 by Houghton Mifflin Company. Published by Houghton Mifflin Company.
Van Laere: EP 1633211 B1; WO 2004/110178 (Dec. 23, 2004 Gazette 2004/52).
Third Party Observations issued Mar. 3, 2011 in Europe Application No. 06781205.7.
"Liquid Filling Viscosity Chart", http://www.apackaging.com/viscosity-chart, Mar. 3, 2011, 1 page.
Lindsay Strowd, et al., "Dysphagia Dietary Guidelines and the Rheology of Nutritional Feeds and Barium Test Feeds", Chest, vol. 133, No. 6, Jun. 2008, pp. 1397-1401.
"Model BII Viscometer", Toki Sangyo, Mar. 3, 2011, 6 pages.
Office Action mailed Jun. 26, 2012, in Japanese Patent Application No. 2007-533132, filed Jun. 6, 2012 ((with English-language Translation).
Masaki Nishio, Department of Speech/Language Pathology and Audiology, International University of Health and Welfare, Rigakuryoho Kagaku 16 (1): 5-16, 2001. Received Feb. 3, 2001 Evaluation and Treatment for Swallowing Disorder (with partial translation).
Office Action issued in corresponding Chinese Application No. 201210246234.5 mailed Aug. 9, 2013, with Partial English Search Report, 7 pp.
Notice of Allowance mailed Oct. 11, 2013 in corresponding U.S. Appl. No. 12/038,290, 20 pp.

* cited by examiner

NUTRIENT COMPOSITION

CROSS-REFERENCE TO RELATED APPLICATION

This application is a continuation of U.S. patent application Ser. No. 12/038,290, filed Feb. 27, 2008, which, in turn, is a continuation of International Application No. PCT/JP2006/314192, filed Jul. 18, 2006, the disclosures of which are incorporated herein by reference in their entireties. This application claims priority to Japanese Patent Application No. 2005-248187, filed Aug. 29, 2005, the disclosure of which is incorporated herein by reference in its entirety.

BACKGROUND OF THE INVENTION

1. Field of the Invention

The present invention relates to a novel nutrient composition, more particularly a nutrient composition being a liquid or semisolid composition containing a specific amount of a protein, the composition having a particular volume-based median size and containing water-insoluble particles having a protein insolubilized by a divalent cation as the major component thereof.

2. Description of the Related Art

The six majour nutrients essential for providing a healthy life style are carbohydrates, proteins, lipids, inorganic salts (minerals), vitamins, and dietary fibers. These nutrients are generally ingested through the regular diet. However, a nutrient composition collectively containing the nutrients is required by elderly persons who have difficulty masticating and swallowing due to cerebral vascular disorder, neuromuscular disorder, or the like, patients who have difficulty in oral intake due to consciousness disorder, postoperative patients, or the like. Although a concentrated liquid food is exemplified as such a nutrient composition, intake of such a liquid food may cause aspiration pneumonia in elderly persons with a reduced swallowing and mastication ability, in particular. Moreover, in the case of elderly persons with a reduced stomach size, the possible amount of food-intake thereof is extremely small. Accordingly, high-calorie nutrient compositions containing the necessary quantity of each nutrient, such as, proteins, minerals, and the like, are demanded by medical practice, and most available nutrient compositions are prepared to have a calorie density of 1 kcal/ml or more.

Most conventionally available fluid diets and nutritional supplements have a calorie density of 1 to 2 kcal/ml (a specific gravity of 1.07 to 1.14). Among them, there are nutrient compositions with a calorie density of 1 to 1.5 kcal/ml, the nutrient compositions independently enabling nutritional management (of bedridden elderly person, in particular). Such nutrient compositions are considered to be favorable formulation forms of enteral alimentation for achieving nutritional maintenance in persons administered them by tubal administration as well as oral intake.

However, in a conventionally available high-calorie nutrient composition of over 1.5 kcal/ml, the formulation amount of proteins or minerals is small with respect to the total energy of the nutrient composition, and therefore intake thereof only cannot maintain favorable nutrition conditions. In particular, an estimated average quantity of proteins necessary for persons aged over 70 is 40 to 50 g/day (Food intake standard in Japan, 2005). However, the formulation amount of the proteins is required to be preferably 6% or more, more preferably 7.5% or more, so that bedridden elderly persons intake the estimated average necessary quantity of proteins in almost 1,000 kcal/day, which is a practical energy intake amount.

Although a nutrient composition with high protein is known (Patent Document 1), the nutrient composition mainly aims to maintain favorable flavor with a high protein content, and the formulation amounts of other nutrients, particularly, minerals, such as sodiums, potassiums, calciums, magnesiums, or the like, are not considered to fully meet the above-mentioned food intake standard from the standpoint of emulsion stability.

In order to produce nutrient compositions which contain fats and oils and proteins and can be stored for a long time, emulsification is required to be performed using a high-pressure homogenizer, high-speed stirrer, or the like. However, in the case where a formulation liquid containing a large amount of such nutrients and minerals is prepared, the viscosity thereof is significantly increased, and thereby dissolution and formulation efficiencies of the raw materials decreases, and emulsification and sterilization treatments become difficult. Moreover, if the viscosity of the nutrient composition is increased, adhesive properties thereof are also increased, as a result of which the nutrient composition tends to adhere to and remain in the mouth or tube at the time of oral or tubal intake thereof, and therefore the nutrient composition does not easily enter the body.

In recent years, as an aspect of tubal intake, a method of tubal provision of nutrition through gastric fistula or enteroproctia has spread. The method of tubal provision of nutrition through gastric fistula or enteroproctia is a method in which a nutritional supplement is continuously or intermittently administered through a tube placed in an external fistula (fistulous opening) operatively or endoscopically formed in the esophagus, the stomach, or the jejunum (most of which is the stomach), to directly supply the nutritional supplement to the stomach or the intestine. Accordingly, such a method enables patients to ingest moisture and nutrition through the alimentary canal in the same way as that of healthy persons, and thereby the quality of life (hereinafter, abbreviated as QOL) of the patients is considered to be improved. Even in the case of the method of tubal provision of nutrition through gastric fistula or enteroproctia, if the viscosity of the nutrient composition is high and the adhesive properties thereof are strong at the time of administering the nutrient composition into the stomach or the intestine through a tube, the nutrient composition cannot be easily administered.

Thus, if the nutrient composition is administered to the patient, particularly through a tube, it is preferable that the viscosity-increase of the nutrient composition be suppressed and the adhesive properties inside the tube be reduced to make it possible for the nutrient composition to be administered by applying as small a pressure as possible. Although a method in which a protein hydrolysate, such as a peptide or amino acid, is formulated is conventionally proposed to suppress the viscosity-increase of the nutrient composition, and such a low-molecular weight protein material is generally known to promote emulsification degradation of fats, which results in the viscosity-decrease, problems such as emulsification destabilization or browning occurring caused by promotion of aminocarbonyl reaction arise.

Thus, it is quite difficult to prepare a nutrient composition with a high protein content easily-administerable for patients in various administration manners by uniformly dispersing, as an emulsion, the nutrient composition in water, a dispersion medium, without deteriorating the taste and flavor thereof.

Patent Document 1: Japanese Laid-Open Patent Application, No. 2004-97119.

SUMMARY OF THE INVENTION

The present invention relates to a nutrient composition containing at least a carbohydrate, a lipid, a protein, and a mineral, the nutrient composition being a liquid or a semi-solid, characterized in that the volume-based median size (d50) of particles in the nutrient composition is 5 to 100 μm, and water-insoluble particles containing a protein insolubilized by a divalent cation as the major component thereof are contained in the nutrient composition.

It is preferable that the average particle size of the particles in the nutrient composition be 400 μm or less.

It is preferable that the volume-based median size (d50) of the water-insoluble particles in the nutrient composition be 10 to 100 μm.

Also, the present invention relates to a nutrient composition containing at least a carbohydrate, a lipid, a protein, and a mineral, the nutrient composition being a liquid or a semi-solid, wherein water-insoluble particles containing a protein insolubilized by a divalent cation as the major component thereof are contained in the nutrient composition, and the mass of the protein with respect to the total moles of divalent ions forming the water-insoluble particles is 1.5 to 3 g/mmol.

It is preferable that the viscosity of the nutrient composition held at 25° C. be 400 to 7,000 mPa·s. It is more preferable that the viscosity of the nutrient composition held at 25° C. be 1,000 to 7,000 mPa·s.

It is preferable that the viscosity of the nutrient composition held at 37° C. for 30 minutes after being held at 25° C. be 200 to 3,000 mPa·s.

It is preferable that the calorie content of the nutrient composition be 1.5 to 2.2 kcal/g, the protein content thereof be 7 to 14% by mass, the lipid content thereof be 3 to 7% by mass, the carbohydrate content thereof be 20 to 35% by mass.

It is preferable that the nutrient composition further contain 0.05 to 2.0% by mass of a free glutamic acid.

The nutrient composition may be a composition having a promoting action on gastric emptying.

The nutrient composition may be an enteral composition.

The nutrient composition may be a gastrointestinal-therapeutic composition.

The nutrient composition may be a malnutrition-therapeutic composition.

The nutrient composition may be a reflux esophagitis-prophylactic/therapeutic composition.

The nutrient composition may be an aspiration pneumonia-prophylactic/therapeutic composition.

DETAILED DESCRIPTION OF THE INVENTION

Figure 1:
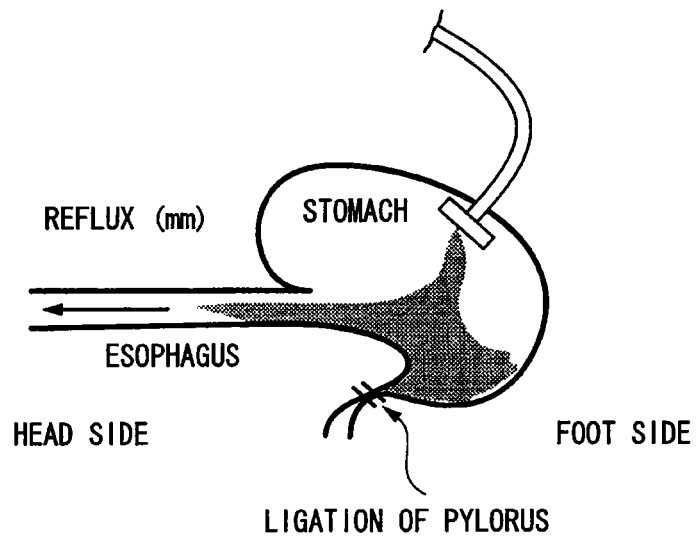
FIG. 1 is a schematic drawing illustrating a method of a gastroesophageal reflux test performed in Test Example 3.

An object of the present invention is to provide a nutrient composition with a high protein content, containing necessary nutrients other than the protein in suitable quantities, being introducible simply and easily into the patients in various administration manners, being excellent in heat-resistance for sterilization, and storage stability, and being massively producible at low cost without requiring any complicated production units or steps. In particular, an object of the present invention is to provide a nutrient composition with rheologic properties favorable for oral intake or tubal administration even if the formulation amount of the proteins or minerals is increased. More specifically, an object of the present invention is to provide a high-calorie nutrient composition of over 1.5 kcal/ml, for example, containing a sufficient amount of the proteins and minerals, the conventional formulation amount of the proteins and minerals being insufficient in the case where energy intake is 1,000 kcal/day, the nutrient composition being free from any problems in terms of production, distribution, and utilization thereof.

As a result of intense investigation by the present inventors to solve the above-mentioned problems, the present inventors focused their attention on the form of a protein and the volume-based median size of a nutrient composition. In order to prevent separation of fats and precipitation of other nutrient components, a protein raw material is conventionally prepared based on the premise that the protein raw material is microparticulated or homogenized even if the viscosity is increased. The nutrient composition according to the present invention exhibits favorable rheologic properties without increasing the viscosity or the adhesive properties by making the particular size be within a constant range even in a non-uniform state without depending on conventional microparticulation or homogenization of the protein. Accordingly, the nutrient composition according to the present invention can be continuously filled easily in a container, can be simply and easily administered to the patients in various administration manners, exhibit excellent heat-resistance for sterilization and storage-stability, and substantially maintain a homogeneous condition. In order to make the particle size in the nutrient composition with a high protein content be within a preferable range, each protein raw material is made to exist therein in the form of particles insolubilized with a divalent cation.

That is, the present invention provides a nutrient composition containing at least a carbohydrate, a lipid, a protein, and a mineral, the nutrient composition being a liquid or a semi-solid, characterized in that the volume-based median size (d50) of particles in the nutrient composition is 5 to 100 μm, and water-insoluble particles containing a protein insolubilized by a divalent cation as a major component thereof are contained in the nutrient composition.

Also, the present invention provides a nutrient composition containing at least a carbohydrate, a lipid, a protein, and a mineral, the nutrient composition being a liquid or a semi-solid, in which water-insoluble particles containing a protein insolubilized by a divalent cation as a major component thereof are contained in the nutrient composition, and the mass of the protein with respect to total moles of divalent ions forming the water-insoluble particles is 1.5 to 3 g/mmol.

In the following, the nutrient composition according to the present invention will be explained in more detail.

It is preferable that the content of the protein in the nutrient composition according to the present invention be 7 to 14% by mass. If the content is 7 to 14% by mass, a nutrient composition with high-calorie and high-protein can be prepared. That is, if the calorie is 1.5 to 2.2 kcal/g, the necessary quantity, 40 to 50 g/day, of protein for elderly persons aged over 70 can be supplied by the nutrient composition alone. Examples of the protein include casein, salts thereof, milk proteins such as whey, soybean proteins, wheat proteins, corn proteins, fish proteins, egg proteins, and the like. These may be raw materials processed in a form of powder, granules, flakes, or pellets. At least one kind is selected from the above to be used in the present invention. Among them, at least the casein or the salt thereof is preferably formulated in an amount of 2 to 8% by mass, because the particle size of water-insoluble particles can be easily controlled in such a case. Also, hydrolysates of the above-mentioned protein raw materials or amino acids may be formulated as protein-supplying materials. Not all of the proteins and the protein-supplying materials are required to be insolubilized, and insolubilized materials and dissolved materials may exist at various ratios depending on the needs of a formulation composition. It is preferable that the content of free glutamic acids in the nutrient composition be 0.05 to 2.0% by mass, the free glutamic acids being materials originating from the protein source used according to the present invention, that is, protein raw materials, peptide raw materials, or amino acid raw materials.

As the carbohydrate, at least one is selected from monosaccharides such as glucose and fructose, disaccharides such as sucrose and maltose, oligosaccharides, dextrins, starches, sugar alcohols, polysaccharide thickeners, water-soluble dietary fibers, insoluble dietary fibers, and the like. It is preferable that the content of the carbohydrate in the nutrient composition according to the present invention be 20 to 35% by mass.

As the lipid, at least one is selected from canola oils, soybean oils, corn oils, perilla oils, safflower oils, palm oils, other fats and oils originating from vegetables, fish oils, butters, lard oils, other fats and oils originating from animals, emulsifying agents containing fatty acids in their structure, and functional fats and oils such as triglycerides of medium-chain fatty acid. It is preferable that the content of the lipid in the nutrient composition according to the present invention be 3 to 7% by mass.

As the mineral, minerals essential as nutritional components, such as, for example, sodium, potassium, calcium, magnesium, phosphorus, chlorine, iron, zinc, copper, and manganese are exemplified. As the divalent cation, ions of the above-mentioned nutrients, that is, calcium, magnesium, iron, zinc, copper, manganese, and the like are exemplified, and at least one selected from inorganic salts thereof and organic acid salts thereof may be used as a raw material. The mass of the protein with respect to the total moles of divalent ions forming the water-insoluble particles is 1.5 to 3 g/mmol, preferably 2 to 3 g/mmol. Preferably, either a calcium ion or a magnesium ion is made to exist as a divalent cation in a preparation liquid to which the protein raw material is to be added. More preferably, both the calcium ion and the magnesium ion are made to exist, and the water-insoluble particles are formed so that the mass of the protein with respect to the total moles of the calcium and magnesium is 1.5 to 3 g/mmol. By making the divalent ions and the protein form the water-insoluble particles in the above-mentioned ratio, the volume-based median size (d50) of the particles contained in the composition falls within a preferable range, and favorable rheologic properties are realized without increasing the viscosity and adhesive properties of the composition.

If the amount of polyanions counter to a sodium ion or potassium ion, such as, for example, a sulphate ion, carbonate ion, phosphate ion, or organic acid ion, is extremely great in comparison with the amount of the divalent cations, the divalent cations and the polyanions form insoluble salts and then precipitate, as a result of which agglomeration of the protein proceeds with difficultly, and white precipitates tend to be produced in storage. Accordingly, it is preferable that the amount of the polyanion be small in view of the above. However, it is preferable that the amount of the polyanion be determined in view of adjustment of optimum pH, realization of favorable flavor, the viscosity, and formulation of the nutritional components.

In the present invention, the phrase "water-insoluble particles containing an insolubilized protein as the major component thereof" refers to particles which are easily precipitated by centrifuging at 3,000 rpm, for example. It is preferable that the precipitated particles have a volume-based median size (d50) of 10 to 100 µm, more preferably 10 to 30 µm. If the volume-based median size exceeds 100 µm, a rough feeling at the time of oral intake tends to increase. If the volume-based median size is less than 10 µm, the viscosity tends to increase, and thereby a gummy feeling tends to increase, and the force required to extrude the nutrient composition for tubal administration tends to be extremely high. The insolubilized particles differ from casein calcium dispersing in milk (casein micelle) in that the casein calcium is not easily precipitated even by centrifuging.

In the present invention, the particle size is measured with a laser-scattering type device for measuring particle size. The measurement is performed using a PIDS (polarization intensity differential scattering) assembly, and analysis thereof is performed under conditions in which the refractive index of liquid (suspension part) is 1.32, that of a sample, real part, is 1.45, and that of an imaginary part is 0.

The insolubilized protein particles may be prepared by reacting the protein with the divalent cation, together with the polyanion depending on circumstances, to agglomerate the protein by changing the stereo structure or charge state of the protein. Although the divalent cation may be mixed with the protein as an insoluble or poorly-soluble salt such as a citrate, sulphate, phosphate, carbonate, or the like, the divalent cation is preferably mixed with the protein as a solution of readily-soluble salt, such as a lactate, hydrochloride, or the like. By adding the divalent cation as a solution, the protein dissolving and dispersing is prevented from suddenly reacting to form coarse particles. Also, it is preferable that the divalent cation and the protein be gradually added and mixed, and also the protein solution be rapidly stirred for mixing. The rapid stirring is performed by stirring it at 5000 rpm or less.

Moreover, it is preferable that the monovalent cation, protein, and divalent cation, be mixed in this order. If the monovalent cation, divalent cation, and protein are mixed in this order, a large amount of insoluble salts tends to be produced depending on molar ratio and concentration of the polyanion and the divalent cation in the formulation liquid.

In the present invention, the protein may form a complex with the lipid, carbohydrate, or the like, provided that the water-insoluble particles contain the protein as the major component thereof. The insolubilized components of the lipid, protein, and salts of the divalent cation may exist independently or as complexes.

It is preferable that the volume-based median size (d50) of the nutrient composition according to the present invention be 5 to 100 µm, more preferably 20 to 50 µm. Although the volume-based median size (d50) of the water-insoluble particles containing the insolubilized protein as the major component thereof is preferably 10 to 100 µm, as described above, fat globule particles exist in addition to the water-insoluble particles in the nutrient composition. The volume-based median size (d50) of all of these particles is 5 to 100 µm.

In accordance with the growth of the insolubilized particles, the viscosity of a preparation liquid decreases, and then a nutrient composition with an arbitrary particle size distribution is prepared. If the volume-based median size (d50) is less than 5 µm, the viscosity-decrease is recognized, however, neither the viscosity nor the adhesive properties of the nutrient composition are sufficient to realize favorable fluidity in a tube. In contrast, if the volume-based median size (d50) exceeds 100 μm, the uniformity of many effective ingredients, such as the protein, in a nutrient composition are not realized in a preparation process, and a rough feeling thereof during oral intake is significant. Accordingly, such a nutrient composition is not favorable in terms of flavor and swallowing. Moreover, clogging of a tube may often occur at the time of tubal administration.

It is preferable that the average particle size of the particles in the nutrient composition according to the present invention be 400 μm or less, more preferably 5 to 200 μm. In the case where the average particle size is within the above-mentioned range, even if particles, other than the insolubilized particles, with a particle size of over 100 μm are contained in the nutrient composition, the nutrient composition can be used without problems in terms of flavor and fluidity in a tube, provided that the volume-based median size (d50) does not exceed 100 μm.

It is preferable that the viscosity of the nutrient composition be moderately high, since easy separation of the insolubilized particles in the nutrient composition left still may deteriorate the commercial value thereof, and, even if the nutrient composition is separated, it is preferable that easy redispersion and difficult reseparation be realized so as to prevent aspiration pneumonia in elderly persons with a decreased swallowing and mastication ability. In contrast, if the viscosity is extremely high, oral or tubal intake is difficult and the residual volume in a tube increases. Accordingly, it is preferable that the viscosity of the nutrient composition at 25° C. be 400 mPa·s or more, more preferably 1,000 mPa·s or more, and be 7,000 mPa·s or less, more preferably 3,000 mPa·s or less. In particular, if the viscosity is 1,000 to 7,000 mPa·s, oral or tubal intake is easy, the residual volume in a tube decreases, washing efficiency of the tube is improved, and the occurrence of reflux esophagitis and aspiration pneumonia is prevented.

As used herein, the term "viscosity" refers to a value obtained by measurement in a fluid form for oral or tubal intake. The form of the nutrient composition before intake may not be a liquid. For example, the form of the nutrient composition may be a semisolid that shows fluidity when a non-fluid structure, such as a pudding or jelly, is broken by applying external force before intake. The viscosity is measured using a rotary viscometer with a No. 3 rotor at 12 rpm and 25° C. (hereinafter, the same).

The viscosity may also be adjusted using a thickener or a gelling agent. Examples of the above-mentioned viscosity modifier include an agar, carageenan, furcellaran, alginate, gelatin, pectin, mannan, gellan gum, cassia gum, locust bean gum, arabic gum, tara gum, guar gum, xanthan gum, starch, and the like. These may be used alone or in combination of plural kinds thereof. Among them, the agar is preferably used as a gelling agent to make the nutrient composition according to the present invention have plastic flow characteristics which allow the nutrient composition to flow when the shear stress exceeds the yield value. As a result, a favorable nutrient composition for tubal provision of nutrition through gastric fistula or enteroproctia is provided, the composition being free from characteristics of conventional nutrient compositions, that is, high-viscosity and high-adhesive properties exhibited at the time of tubal provision of nutrition to the stomach or the intestine through gastric fistula or enteroproctia. In more detail, it is preferable that the gel strength be appropriately adjusted by adding the gelling agent to prevent occurrence of reflux stomach/esophagus inflammation, decrease frequency of diarrhea, and also prevent leak of the nutrient composition from an implantation site in the abdominal cavity, the implantation site being used for tubal provision of nutrition through gastric fistula or enteroproctia. As a result, the pressing force required for feeding the nutrient composition into the stomach through a tube or a connection adaptor for gastric fistula from a high-capacity syringe or a pouch with a plug, the syringe or pouch being filled with the nutrient composition, for example, is small, and therefore the nutrient composition can be easily administered even by elderly persons, which results in a reduction of the caring-burden on nurses in home care.

It is preferable the viscosity of the nutrient composition according to the present invention be 200 to 3,000 mPa·s, when the viscosity is measured after the nutrient composition is held at 25° C. and then further held at 37° C. for 30 minutes. Such a viscosity promotes emptying of the stomach while preventing reflux into the esophagus when the nutrient composition according to the present invention is introduced into the stomach, and thus contributes to making the nutrient composition be further favorable for elderly persons with swallowing and mastication abilities reduced by cerebral vascular disorder, neuromuscular disorder, or the like, or patients with difficulty in oral intake due to consciousness disorder, or the like.

In the nutrient composition according to the present invention, other essential nutrients, such as vitamins or dietary fiber, or functional food materials such as catechin, carnitine, coenzyme Q, GABA, or α-lipoic acid, may be formulated in addition to the above-mentioned raw materials. Also, raw materials or extracts originating from foods, or food additives such as seasonings, coloring agents, sweetening agents, flavors, or pH modifiers, may be formulated so as to improve taste.

The pH of the nutrient composition varies depending on kinds or intake-forms of the raw materials used. Most of the protein is generally denatured by a decrease of the pH, and thereby agglomeration and precipitation are caused to produce an almost insolubilized state. However, it is preferable that the pH of the nutrient composition be adjusted to 4.8 to 7.2, more preferably 5.6 to 6.6, in order to realize favorable conditions of the water-insoluble particles according to the present invention, in which the volume-based median size (d50) is 10 to 100 μm and the particles have difficulty separating during storage.

The viscosity of the nutrient composition according to the present invention is significantly decreased by insolubilizing the protein, and effects thereof are exhibited for a high-calorie composition. A composition with a calorie content of 1.5 to 2.2 kcal/g in which the ratio of energy from the protein is 20 to 25% is favorable. In such a case, the content of the protein is preferably 7 to 14% by mass. Also, if the ratio of energy from the lipid is 20 to 30%, the content of the lipid is 3 to 7% by mass, which is favorable for the nutrient composition. Such an appropriate mixing of the protein and the lipid contributes to providing a preferable nutrient composition free from problems in terms of nutrition supply and separation of oil during storage.

Next, a process for preparing the nutrient composition according to the present invention will be explained.

First, a carbohydrate is added to water preferably heated at 60° C. or more, and then a salt containing a monovalent cation is mixed therewith. Fats and oils, and, as needed, an emulsifying agent, are mixed with the mixture, and then the protein is further mixed therewith and stirred to disperse and dissolve the protein. A salt containing a divalent cation is mixed with the solution, and stirred to insolubilize the protein. If needed, a vitamin, dietary fiber, flavor, or the like is mixed with the resultant and stirred. Then, water is added to the resultant to adjust the volume thereof to a required degree. In the mixing steps or mixture-treatment steps, an emulsification process performed generally using a high-pressure homogenizer, ultrasonic emulsifier, colloid mill, high-speed homomixer, or the like, is not always required. The reason for this derives from the novel preparation method in which oil droplets are made to assemble and agglomerate by including the oil droplets in the insolubilized protein particles or making the oil droplets interact with the insolubilized protein particles, such a state of the oil droplets being different from that in conventional fluid diets in which the oil droplets disperse as fine emulsions in water thereof. The process using the high-speed homomixer is performed by stirring at 5,000 rpm or more.

After adjusting the volume, the resultant is subjected to heat sterilization and then put into a container, or the resultant is put into a container and then subjected to heat sterilization. The heat sterilization treatment enables long storage. As a method for sterilization, Ultra High Temperature short-time (UHT) sterilization, hot-water sterilization, sterilization using a batch-type or continuous-type retort apparatus, or the like may be adopted. Among these, one or plural processes may be adopted, as needed.

Commercially available high-calorie liquid foods with a calorie density of over 1.5 kcal/ml are produced by an aseptic packaging system in which the UHT sterilization is performed or a method in which proliferation of microorganisms is suppressed by decreasing pH and heat-sterilization conditions are made to be moderate. That is, the nutrient composition according to the present invention is prepared by a preparation method adopted for preventing significant emulsion breakage-promotion caused by treating at high temperature for a long time.

The retort-type in which sterilization is performed at a high temperature for a long time may be adopted for the nutrient composition according to the present invention. According to the novel preparation method based on protein-insolubilization, damage to preparations by agglomeration and coalescence of fine emulsions is not always required to be suppressed. The nutrient composition according to the present invention may be packed in a container with various shapes, and then subjected to the retort-sterilization to supply to users.

Although the nutrient composition according to the present invention may be used for oral or tubal intake, the nutrient composition according to the present invention is particularly suitable for enteral administration. Also, since the nutrient composition according to the present invention has an appropriately-adjusted viscosity and contains essential nutrition sources in a well-balanced state, the nutrient composition is suitable for gastrointestinal-therapy for elderly persons of which the stomach size is reduced with age, patients with lowered swallowing and mastication abilities due to cerebral vascular disorder, neuromuscular disorder, or the like, patients with difficulty in oral intake due to consciousness disorder, postoperative patients, or the like, therapy for patients with malnutrition conditions, or prevention or therapy of reflux esophagitis or aspiration pneumonia. For each patient described above, formulation of 0.05 to 2% by mass of a free glutamic acid in the nutrient composition promotes gastric emptying thereof, which contributes to providing a favorable nutrient composition.

The nutrient composition according to the present invention is significantly prevented from a viscosity-increase caused by high-concentrations of the dissolving protein, since the protein therein is insolubilized. Also, the lipid exists in a state different from that of emulsions in conventional fluid diets, which provides benefits in preparation (1); benefits in intake and administration (2); and benefits in nutritional constitution (3). In the following, each benefit will be explained.

As the benefits in preparation (1), increase of efficiency of dissolving and mixing the raw materials in the formulation step, and increase of yield rate by decreasing adherence of the formulation liquid in a tank are expected. In the packaging step into the container, suppression of viscosity-increase prevents dripping discharge of liquid from a filling nozzle, as a result of which malfunction of sealing caused by liquid entering during sealing is prevented. In the sterilization step, various sterilization methods may be adopted, which decrease necessary restrictions in manufacturing facilities and thereby equipment investment is reduced. In the retort-sterilization step, the thermal conductivity increases in accordance with the viscosity-decrease, which results in a decrease of time required for sterilization, and thereby browning of the nutrient composition and deterioration of the vitamin can be suppressed.

As the benefits in intake and administration (2), "surface tackiness" derived from the protein at the time of oral intake is reduced, and the feeling of remaining in the mouth is reduced, as a result of which unpleasantness at the time of ingestion is reduced. In the case of tubal administration, the force required for extrusion is small. In particular, such effects are largely exhibited at the time of administration from the gastric fistula or enteroproctia fistula. Although conventional fluid diets (several to several ten mPa·s) are forced to be administered for a long time due to a possibility of occurrence of diarrhea or gastroesophageal reflux, the nutrient composition according to the present invention suppresses such unfavorable occurrence due to having a viscosity of several thousand mPa·s, and enables easy injection thereof for a short-time, and therefore the nutrient composition is expected to greatly contribute to improvement of the QOL of the patient and increase the working efficiency in a caring and nursing site.

As the benefits in nutritional constitution (3), formulation of the protein and minerals, particularly, sodium, potassium, calcium, or magnesium, at a high concentration is possible. Since the protein exists in an insolubilized state, and the lipid also disperses in a state different from that of emulsions in conventional fluid diets, there is almost no need to pay attention to emulsification breakage caused by the minerals. Thus, the nutrient composition according to the present invention can be prepared as a low-weight and high-calorie preparation, and enables nutrition such as the protein and minerals to be easily supplied to persons with a reduced stomach capacity, such as elderly persons, in particular.

As described above, the nutrient composition according to the present invention is a nutrient composition with a high protein content containing necessary nutrients in suitable quantities, the nutrient composition being administered simply and easily into the patient in various administration manners, being excellent in heat-resistance for sterilization and storage-stability, and being massively producible at low cost without requiring any complicated production units or steps.

EXAMPLES

In the following, the present invention will be explained in more detail by illustrating some examples. However, the present invention is not limited to the following examples.

Example 1

As described below, 4,000 g of a formulation was prepared. The formulation amount of each raw material is shown in Tables 1 to 3. 1,420 g of water for formulation was put into a 5 L-stainless-steel bucket, and heated at 70 to 80° C. in a water bath. Then, a dextrin, granulated sugar, sodium ferrous citrate, sodium phosphate, potassium phosphate, tripotassium citrate, and sodium gluconate were dissolved using T. K. ROBOMIX (trademark, manufactured by Tokusyu Kika Kogyo Co., Ltd.) under high-speed stirring conditions at 3,000 rpm. To the solution, a mixture liquid prepared by mixing and dissolving an edible fat and oil and an emulsifying agent at 70 to 80° C. was then added. To the mixture, a milk protein source raw material (manufactured by Fonterra Ltd.: with a casein content of 66.8% by mass), sodium glutamate, mineral yeast mix, and flavor were added in this order, and then uniformly dissolved and dispersed therein. To the resultant, a dissolved water-soluble dietary fiber, calcium lactate, and magnesium chloride were gradually added. Then, a vitamin mix, sodium ascorbate, and sodium erythorbate were added to the resultant, and dispersed and dissolved therein. Remaining raw materials were added to the resultant and weighed to add water until the mass of the resultant reached 4,000 g. Then, dissolving and dispersing were performed until uniform conditions were realized, and the resultant was aliquoted into aluminum pouches (each with a spout) in an amount of 150 g per pouch, followed by performing retort-sterilization at 110° C. and 126° C. in a two-stage heat sterilization procedure. The obtained samples were stored at 25° C., and, on the day following the sterilization, the viscosity thereof, measured using a rotary viscometer (BH-80 (product name), manufactured by TOKI SANGYO CO., LTD.) with a rotor No. 3, at 12 rpm, was confirmed to be approximately 2,000 mPa·s (at 25° C.). Also, the median size measured using LS 13 320 (product name, manufactured by Beckman Coulter, Inc.) was confirmed to be 23 μm.

TABLE 1

| Raw material | Formulation amount (g) |
| --- | --- |
| Milk protein source raw material | 416 |
| Sodium glutamate | 24 |
| Dextrin | 1040 |
| Granulated sugar | 68 |
| Soluble dietary fiber | 117 |
| Sodium phosphate | 10.4 |
| Potassium phosphate | 9.2 |
| Magnesium chloride | 23.6 |
| Calcium lactate | 12.8 |
| Tripotassium citrate | 24.0 |
| Sodium gluconate | 80.0 |
| Sodium ferrous citrate | 0.84 |
| Mineral yeast mix | 3.3 |
| Vitamin mix | 2.6 |
| Sodium ascorbate | 2.2 |
| Sodium erythorbate | 2.2 |
| Flavor | 4.0 |
| Edible fat and oil | 213 |
| Emulsifying agent | 11.2 |

TABLE 2

Constitution of vitamin mix

| Raw material | Formulation amount (mg) |
| --- | --- |
| Vitamin A powder (175,000 IU/g) | 80 |
| β-carotene (1.5% powder) | 360 |
| Vitamin D3 powder (200,000 IU/g) | 4.5 |
| Vitamin E powder (20% d-α-Toc) | 102 |
| Vitamin K2 (0.2% powder) | 60 |
| Thiamine hydrochloride | 7.4 |
| Pyridoxine hydrochloride | 5.3 |
| Riboflavin sodium phosphate | 5.2 |
| Nicotinic-acid amide | 40 |
| Calcium pantothenate | 28 |
| Cyanocobalamin (0.1% powder) | 4.7 |
| Folic acid | 0.7 |
| Biotin yeast (50 mg/100 g) | 1068 |

TABLE 3

Constitution of mineral yeast mix

| Raw material | Formulation amount (mg) |
| --- | --- |
| Zinc yeast | 1492 |
| Copper yeast | 748 |
| Selenium yeast | 266.8 |
| Manganese yeast | 724 |
| Iodine yeast | 92.4 |

Example 2

As described below, 4,000 g of a formulation was prepared. The formulation amount of each raw material is shown in Table 4. 1,600 g of water for formulation was put into a 5 L-stainless-steel bucket, and heated at 70 to 80° C. in a water bath. Then, a dextrin, granulated sugar, water-soluble dietary fiber, sodium ferrous citrate, zinc gluconate, copper gluconate, sodium phosphate, sodium metaphosphate, potassium phosphate, tripotassium citrate, sodium gluconate, and sodium chloride were dissolved using T. K. ROBOMIX (trademark, manufactured by Tokusyu Kika Kogyo Co., Ltd.) under high-speed stirring conditions at 2,000 rpm. To the solution, a mixture liquid prepared by mixing and dissolving an edible fat and oil and an emulsifying agent at 70 to 80° C. was then added. To the mixture, a milk protein source raw material (manufactured by Fonterra, Campina: with a casein content of 20.8% by mass), sodium glutamate, and flavor were added in this order, and then uniformly dissolved and dispersed therein. To the resultant, a powdered agar was added and sufficiently swollen, followed by heating at 85° C. to dissolve the agar, and then gradually adding a dissolving and dispersing calcium lactate, magnesium chloride, and calcium carbonate thereto. Then, sodium ascorbate and sodium erythorbate were added to the resultant and dispersed and dissolved. The mass of the resultant was weighed to add water until the mass thereof reached 4,000 g. Then, dissolving and dispersing were performed until uniform conditions were realized, and the resultant was aliquoted into aluminum pouches (each with a spout) in an amount of 150 g per pouch, followed by performing retort-sterilization at 110° C. and 126° C. in a two-stage heat sterilization procedure. The obtained samples were stored at 25° C., and, on the day following the sterilization, the viscosity thereof, measured using a rotary viscometer (BH-80, manufactured by TOKI SANGYO CO., LTD.) with a rotor No. 3, at 12 rpm, was confirmed to be approximately 7,000 mPa·s (at 25° C.). Also, the sample was diluted twice and then heated at 80° C. to dissolve the agar, and then the median size thereof was measured using LS 13 320 (product name, manufactured by Beckman Coulter, Inc.). The median size thereof was 12 μm.

TABLE 4

| Raw material | Used amount | Unit |
| --- | --- | --- |
| Milk protein source raw material | 370 | g |
| Sodium glutamate | 20 | g |
| Dextrin | 1016 | g |
| Granulated sugar | 68 | g |
| Soluble dietary fiber | 96.8 | g |
| Potassium phosphate | 7.8 | g |
| Sodium phosphate | 6.4 | g |
| Sodium metaphosphate | 6.0 | g |
| Tripotassium citrate | 22.4 | g |
| Sodium gluconate | 30.0 | g |
| Sodium chloride | 4.8 | g |
| Magnesium chloride | 20.8 | g |
| Calcium lactate | 17.6 | g |
| Sodium ferrous citrate | 0.72 | g |
| Zinc gluconate | 0.50 | g |
| Copper gluconate | 45.2 | mg |
| Calcium carbonate | 10.0 | g |
| Agar powder | 6.8 | g |
| Sodium ascorbate | 2.0 | g |
| Sodium erythorbate | 2.0 | g |
| Flavor | 4.0 | g |
| Edible fat and oil | 181 | g |
| Emulsifying agent | 20.1 | g |

Example 3

As described below, 4,000 g of a formulation was prepared. The formulation amount of each raw material is shown in Table 5. 1,630 g of water for formulation was put into a 5 L-stainless-steel bucket, and heated at approximately 85° C. in a water bath. Then, a powdered agar was added thereto and dissolved therein. Then, a dextrin, water-soluble dietary fiber, sodium ferrous citrate, zinc gluconate, copper gluconate, sodium phosphate, potassium phosphate, tripotassium citrate, sodium gluconate, and sodium chloride were dissolved in this order using T. K. ROBOMIX (TRADEMARK, manufactured by Tokusyu Kika Kogyo Co., Ltd.) under high-speed stirring conditions at 2,000 rpm. Then, a mixture liquid prepared by mixing and dissolving an edible fat and oil and an emulsifying agent at 70 to 80° C. was added thereto. Then, a milk protein source raw material (manufactured by Fonterra, Campina: with a casein content of 41.8% by mass), sodium glutamate, and flavor were added thereto in this order and mixed therewith to obtain uniform dissolving and dispersing conditions. Then, a dissolving calcium lactate and magnesium chloride were gradually added thereto. Then, sodium ascorbate and sodium erythorbate were added thereto, and then dispersed and dissolved. The mass of the resultant was weighed to add water until the mass reached 4,000 g. Then, dissolving and dispersing were performed until uniform conditions were realized, and the resultant was aliquoted into aluminum pouches (each with a spout) in an amount of 150 g per pouch, followed by performing retort-sterilization at 110° C. and 126° C. in a two-stage heat sterilization procedure. The obtained samples were stored at 25° C., and, on the day following the sterilization, the viscosity thereof, measured using a rotary viscometer (BH-80, manufactured by TOKI SANGYO CO., LTD.) with a rotor No. 3, at 12 rpm, was confirmed to be approximately 6,000 mPa·s (at 25° C.). Also, the sample was diluted twice and then heated at 80° C. to dissolve the agar, and then the median size thereof was measured using LS 13 320 (product name, manufactured by Beckman Coulter, Inc.). The median size thereof was 18 μm.

TABLE 5

| Raw material | Used amount | Unit |
| --- | --- | --- |
| Milk protein source raw material | 340 | g |
| Sodium glutamate | 20 | g |
| Dextrin | 980 | g |
| Soluble dietary fiber | 86.0 | g |
| Potassium phosphate | 7.2 | g |
| Sodium phosphate | 16.0 | g |
| Tripotassium citrate | 20.8 | g |
| Sodium gluconate | 12.0 | g |
| Sodium chloride | 7.2 | g |
| Magnesium chloride | 16.0 | g |
| Calcium lactate | 36.0 | g |
| Sodium ferrous citrate | 0.56 | g |
| Zinc gluconate | 0.38 | g |
| Copper gluconate | 34.4 | mg |
| Agar powder | 10.0 | g |
| Sodium ascorbate | 1.5 | g |
| Sodium erythorbate | 1.5 | g |
| Flavor | 4.0 | g |
| Edible fat and oil | 168 | g |
| Emulsifying agent | 18.6 | g |

Example 4

Samples 1 to 5 containing components shown in Tables 6 to 8 were prepared. In the following, a method for formulating 1,500 kg of raw materials is described. 500 kg of water (at 80 to 90° C.) was put into a formulation tank (hereinafter, abbreviated as A), and then dextrin and granulated sugar were dissolved therein using a powder-dissolving machine. Then, sodium ferrous citrate, potassium phosphate, tripotassium citrate, sodium gluconate, and potassium chloride were dissolved therein. Then, a liquid prepared by mixing and dissolving an edible fat and oil containing vitamin E and an emulsifying agent at 70 to 80° C. was added from a powder-dissolving machine. Then, a milk protein source raw material (manufactured by Fonterra Ltd., with a casein content of 64.8%), sodium glutamate, cocoa powder, mineral yeast mix, and flavor were added from a powder-dissolving machine, and then dissolved and mixed to obtain uniform dissolving and dispersing conditions. Then, a water-soluble dietary fiber, calcium lactate, magnesium chloride, and magnesium sulphate, each being dissolved in water, were gradually added from a powder-dissolving machine. Then, sodium ascorbate, sodium erythorbate, and vitamin mix, each being dissolved in water, were added from a powder-dissolving machine, and then dispersed and dissolved. The mass of the resultant was made to be 1,500 kg, followed by mixing and dissolving to obtain uniform conditions.

After the formulation, 150 g of each resultant was packed in a side gussets aluminum pouch having a spout (with a width of 80 mm, height of 150 mm, and thickness of 25 mm) via a liquid-feeding line using a continuous type filler, and then subjected to retort-sterilization treatment at 126° C. in a one-step heat sterilization procedure. Each obtained sample was stored at 25° C., and then subjected to sterilization treatment. In order that the viscosities of the samples 1 to 4 were different from each other, the rates of adding calcium lactate, magnesium chloride, and magnesium sulphate were varied for preparation of the Samples 1 to 4. Sample 5 was prepared in a similar way to that of Test Example 4 described below, except that a step of dissolving and dispersing a thickener before measuring the weight using a load cell was further performed. The median sizes of the prepared Samples 1 to 5 were measured using LS 13 320 (product name, manufactured by Beckman Coulter, Inc.) and results thereof are shown in Table 9.

TABLE 6

Formulation ratio of raw materials

| Raw material | Formulation amount (kg) per 1,500 kg of composition | | | | |
|---|---|---|---|---|---|
| | Sample 1 | Sample 2 | Sample 3 | Sample 4 | Sample 5 |
| Milk protein source raw material | 156 | 156 | 156 | 156 | 156 |
| Sodium glutamate | 2.1 | 2.1 | 6.3 | 18.9 | 18.9 |
| Edible fat and oil | 70.1 | 70.1 | 70.1 | 70.1 | 70.1 |
| Emulsifying agent | 10.8 | 10.8 | 10.8 | 10.8 | 10.8 |
| Dextrin | 330 | 330 | 330 | 330 | 330 |
| Granulated sugar | 34.7 | 34.7 | 34.7 | 34.7 | 34.7 |
| Soluble dietary fiber | 39.0 | 39.0 | 39.0 | 39.0 | 39.0 |
| Potassium phosphate | 5.0 | 5.0 | 5.0 | 5.0 | 5.0 |
| Calcium lactate | 5.3 | 5.3 | 5.3 | 5.3 | 5.3 |
| Tripotassium citrate | 4.7 | 4.7 | 4.7 | 4.7 | 4.7 |
| Sodium gluconate | 29.3 | 29.3 | 29.3 | 29.3 | 29.3 |
| Magnesium chloride | 3.9 | 3.9 | 3.9 | 3.9 | 3.9 |
| Magnesium sulfate | 5.7 | 5.7 | 5.7 | 5.7 | 5.7 |
| Potassium chloride | 0.90 | 0.90 | 0.90 | 0.90 | 0.90 |
| Sodium ferrous citrate | 0.30 | 0.30 | 0.30 | 0.30 | 0.30 |
| Mineral yeast mix | 2.00 | 2.00 | 2.00 | 2.00 | 2.00 |
| Vitamin mix | 1.40 | 1.40 | 1.40 | 1.40 | 1.40 |
| Fat and oil containing vitamin E | 0.37 | 0.37 | 0.37 | 0.37 | 0.37 |
| Sodium ascorbate | 3.3 | 3.3 | 3.3 | 3.3 | 3.3 |
| Sodium erythorbate | 3.3 | 3.3 | 3.3 | 3.3 | 3.3 |
| Cocoa powder | 9.3 | 9.3 | 9.3 | 9.3 | 9.3 |
| Flavor | 1.5 | 1.5 | 1.5 | 1.5 | 1.5 |
| Thickener | 0 | 0 | 0 | 0 | 1.5 |

TABLE 7

Constitution of vitamin mix

| Raw material | Formulation amount (g) |
|---|---|
| Vitamin A powder | 26.5 |
| β-carotene (1% powder) | 808.1 |
| Vitamin B1 hydrochloride | 16.5 |
| Sodium riboflavin acid ester | 11.9 |
| Vitamin B6 hydrochloride | 6.5 |
| Vitamin B12 (0.1% powder) | 9.2 |
| Vitamin D3 powder | 7.7 |
| Nicotinic-acid amide | 32.7 |
| Folic acid | 1.0 |
| Calcium pantothenate | 27.7 |
| Vitamin K2 (0.2% powder) | 87.6 |
| Yeast powder (50 mg/100 g) | 368.5 |

TABLE 8

Constitution of mineral yeast mix

| Raw material | Formulation amount (g) |
|---|---|
| Ainc yeast | 1219 |
| Copper yeast | 352 |
| Selenium yeast | 92 |
| Manganese yeast | 304 |
| Iodine yeast | 38 |

TABLE 9

| | Median size (μm) |
|---|---|
| Sample 1 | 33.4 |
| Sample 2 | 28.4 |
| Sample 3 | 31.4 |
| Sample 4 | 24.2 |
| Sample 5 | 25.6 |

Example 5

Sample 6 containing components shown in Tables 10 to 12 was prepared. In the following, a method for formulation in a total weight of 1,500 kg is described. 500 kg of water (at 80 to 90° C.) was put in a formulation tank (hereinafter, abbreviated as A), and then dextrin and granulated sugar were dissolved therein using a powder-dissolving machine, followed by dissolving sodium ferrous citrate, potassium phosphate, sodium phosphate, tripotassium citrate, sodium gluconate, and potassium chloride therein. Then, a liquid prepared by mixing and dissolving an edible fat and oil and an emulsifying agent at 70 to 80° C. was added to the resultant from a powder-dissolving machine. Then, a milk protein source raw material (manufactured by Fonterra Ltd., with a casein content of 64.8%), sodium glutamate, mineral yeast mix, and flavor were added to the resultant from a powder-dissolving machine, and then dissolved and mixed to obtain uniform dissolving and dispersing conditions. Then, a water-soluble dietary fiber, calcium lactate, magnesium chloride, and magnesium sulphate, each being dissolved in water, were gradually added from a powder-dissolving machine. Then, a sodium ascorbate, sodium erythorbate, and vitamin mix, each being dissolved in water, were added from a powder-dissolving machine, and then dispersed and dissolved. The mass of the resultant was made to be 1,500 kg, and the resultant was mixed and stirred until uniform conditions were realized.

After the formulation, the resultant was packed in side gussets aluminum pouches each having a spout (with a width of 80 mm, height of 150 mm, and thickness of 25 mm) in an amount of 150 g (setting range: 147 to 155 g) per pouch via a liquid-feeding line using a continuous type filler. In the filling step, continuous filling was realized without causing any problems in manufacturing. Then, retort-sterilization was performed at 115° C. and 126° C. in a two-stage heat sterilization procedure. The obtained sample was subjected to a long-term stability test.

TABLE 10

| Raw material | Formulation amount (kg) |
|---|---|
| Milk protein source raw material | 156 |
| Sodium glutamate | 9.0 |
| Dextrin | 370 |
| Granulated sugar | 39 |
| Soluble dietary fiber | 44 |
| Sodium phosphate | 3.8 |
| Potassium phosphate | 3.5 |
| Potassium chloride | 3.1 |
| Magnesium chloride | 3.9 |
| Magnesium sulfate | 6.0 |
| Calcium lactate | 4.8 |
| Tripotassium citrate | 4.7 |
| Sodium gluconate | 29.3 |
| Sodium ferrous citrate | 0.31 |
| Sodium ascorbate | 0.85 |
| Sodium erythorbate | 0.85 |
| Vitamin mix | 1.16 |

TABLE 10-continued

| Raw material | Formulation amount (kg) |
|---|---|
| Mineral yeast mix | 1.46 |
| Flavor | 1.5 |
| Edible fat and oil | 72 |
| Emulsifying agent | 12 |

TABLE 11

Constitution of vitamin mix

| Raw material | Formulation amount (g) |
|---|---|
| Dry vitamin A (175,000 IU/g) | 80 |
| β-carotene (1% powder) | 360 |
| Dry vitamin D3 (200,000 IU/g) | 4.5 |
| Vitamin E powder (20% d-α-Toc) | 102 |
| Vitamin K2 (0.2% powder) | 60 |
| Thiamine hydrochloride | 7.4 |
| Pyridoxine hydrochloride | 5.3 |
| Riboflavin sodium phosphate | 5.2 |
| Nicotinic-acid amide | 40 |
| Calcium pantothenate | 28 |
| Cyanocobalamin (0.1% powder) | 4.7 |
| Folic acid | 0.7 |
| Biotin yeast (50 mg/100 g) | 467 |

TABLE 12

Constitution of mineral yeast mix

| Raw material | Formulation amount (g) |
|---|---|
| Zinc yeast | 795 |
| Copper yeast | 281 |
| Selenium yeast | 80 |
| Manganese yeast | 272 |
| Iodine yeast | 35 |

Test Example 1

The nutrient composition prepared in Example 1 was evaluated with respect to the fluidity in tubes. A sample was prepared by filling a standing aluminum pouch having a spout (with a width of 97 mm, height of 138 mm, and folded diameter at the bottom of 25 mm) with 150 g of the nutrient composition, and then the sample was connected with a CPPEG connector (product name, manufactured by HANACO MEDICAL Co., Ltd.) to which a gastric-feeding-tube (manufactured by Bird, attached to a bird wizard) was connected. The length of the tube was 13 cm. The content of the sample was extruded by applying pressure to the sample by placing 5 kg of a weight (manufactured by SARTORIUS K.K., with a diameter of 87 mm) thereon for 1.5 minutes while supporting the weight by the hands to prevent the weight from falling off the sample (without applying pressure by the hands). The mass of the extruded content was measured. By way of comparison, TERUMEAL SOFT and TERUMEAL SOFT M (trademark, manufactured by TERUMO CORPORATION), which are commercially available nutrient compositions with high viscosity, were connected to the above-mentioned apparatus, and then subjected to a contents-extrusion test and measurement by the same way as described above. The test was repeated three times. The product temperature and room temperature were set to be approximately 22° C. The tube after the contents-extrusion test was tried to be washed with 20 ml of tap water using a 25 ml-syringe. After the washing, the inside wall of the tube was observed and the efficiency of washing out the composition was evaluated. Results thereof are shown in Table 13. The nutrient composition prepared in Example 1 resulted in large amounts of extrusion and exhibited excellent efficiency of washing the tube. However, the commercially available TERUMEAL SOFT and TERUMEAL SOFT M (trademark, manufactured by TERUMO CORPORATION) resulted in no extrusion, and exhibited unfavorable efficiency of washing the tube.

TABLE 13

| | Extrusion amount (g) | Efficiency of washing tube |
|---|---|---|
| Nutrient composition of Example 1 | 31.2 | ○ |
| TERUMEAL SOFT | 1.5 | Δ |
| TERUMEAL SOFT M | 0 | X |

○: Almost no composition was adhered to the inside wall of the tube.
Δ: A slight amount of the composition was adhered to the inside wall of the tube.
X: A considerable amount of the composition was adhered to the inside wall of the tube.

Test Example 2

Measurement of the particle size of the nutrient composition prepared in Example 1 and analysis of the water-insoluble materials therein were performed. The nutrient composition was diluted by the same mass of water, and put in a 50 ml-centrifuge tube, followed by centrifuging at 3,000 rpm for 10 minutes with a centrifuge (H-103NR (product name), manufactured by KOKUSAN Co. Ltd.). After the precipitate was collected and dispersed again with 40 ml of purified water, centrifugal treatment was performed again by the same way as described above. Two-layer precipitates (hereinafter, the upper-layer precipitate being abbreviated as precipitate A and the lower-layer precipitate being abbreviated as precipitate B) were collected separately, and the particle size, protein content, calcium content, and magnesium content thereof were measured respectively. Results of the measurement of the particle size are shown in Table 14 and results of the measurement of each content are shown in Table 15. It was revealed that the protein content of the nutrient composition prepared in Example 1, with respect to the total mole number of calcium and magnesium, was within a range of 1.5 to 3 g/mmol.

TABLE 14

| Sample | Average particle size (μm) | Cumulative particle size (μm) | | | | |
|---|---|---|---|---|---|---|
| | | <10% | <25% | <50% (Median size) | <75% | <90% |
| Precipitate A | 6.4 | 2.4 | 4.0 | 7.7 | 10.4 | 15.1 |
| Precipitate B | 44.6 | 23.2 | 31.1 | 45.8 | 58.1 | 73.0 |
| Before centrifugal treatment (reference) | 29.6 | 6.7 | 12.9 | 23.4 | 41.6 | 62.7 |

TABLE 15

| Sample | Median size (μm) | Content per 100 g of precipitate (in parentheses, mole numbers are indicated) | | | Total mole number of calcium and magnesium (abbreviated as s) | Protein content ÷ s |
| --- | --- | --- | --- | --- | --- | --- |
| | | Protein | Calcium | Magnesium | | |
| Precipitate A | 6.4 | 11.4 g | 128 mg (3.20 mmol) | 36 mg (1.48 mmol) | 4.68 mmol | 2.43 g/mmol |
| Precipitate B | 44.6 | 14.4 g | 173 mg (4.33 mmol) | 45 mg (1.85 mmol) | 6.18 mmol | 2.33 g/mmol |

Test Example 3

To the nutrient composition prepared in Example 1, water or a thickener (carboxyl methyl cellulose: CMC) was appropriately added to realize six-level viscosities (20, 200, 330, 1,000, 2,000, and 20,000 mPa·s), and then a phenol red pigment (0.05% by mass) was further added thereto to prepare each sample liquid.

As shown in FIG. 1, a SD male rat aged 8 weeks (215 to 265 g) was subjected to gastrostomy and ligation of the pyloric region of the stomach under nembutal anesthesia. Immediately after the ligation, each sample liquid was administered through the gastric fistula (at 2.5 ml per rat). Ten minutes after the administration, the cardia of the stomach was ligated and the stomach and the esophagus were removed without separating them from each other. The removed esophagus was cut open, and NaOH was sprayed thereon, and the length of a portion stained by reaction with the phenol red pigment from the cardia of the stomach was measured to evaluate effects of each sample liquid on the gastroesophageal reflux.

Figure 2:
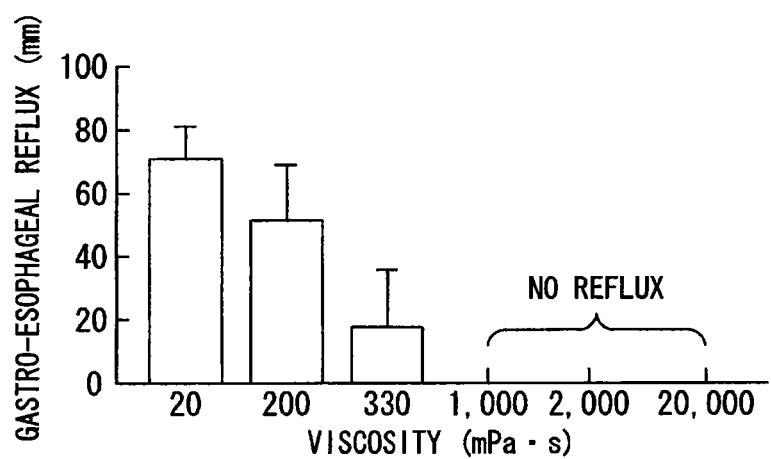
FIG. 2 is a graph showing the relationship between the viscosity of a composition and the gastroesophageal reflux preventabilities thereof (Test Example 3).

Results thereof are shown in FIG. 2. As shown in FIG. 2, the sample liquids with a viscosity of 330 mPa·s or less caused gastroesophageal reflux. In contrast, the sample liquids with a viscosity of over 330 mPa·s, particularly with a viscosity of 1,000 mPa·s or more, did not cause gastroesophageal reflux. That is, it was demonstrated that the nutrient composition having a viscosity of preferably at least 400 mPa·s, more preferably 1,000 mPa·s or more could prevent occurrence of gastroesophageal reflux.

Test Example 4

One week after the sterilization of Samples 1 to 3, or two weeks after the sterilization of Samples 4 and 5, each sample was subjected to sensory evaluation in terms of extrusion properties thereof by the forearm strength required for extrusion, and then the viscosity of the extruded content thereof was measured to evaluate.

Sensory Evaluation.

Sensory evaluation was performed by females in their twenties as described below. Each side gussets aluminum pouch filled with each sample was shaken ten times backward and forward at room temperature (approximately at 25° C.) while gripping the body of the pouch, and then opened. Then, the bung of the side gussets aluminum pouch was connected with a CPPEG connector (product name, manufactured by HANACO MEDICAL Co., Ltd.), and then extrusion was performed two times to evaluate how much forearm strength was required for extrusion in accordance with the following criteria.

⊚: Extrusion was performed quite easily.
○: Although slight forearm strength was required, extrusion was performed easily.

Δ: Although extrusion was performed, forearm strength was required.

Measurement of the Viscosity.

The amount of each sample extruded under constant pressure was evaluated as described below.

A spout of each side gussets aluminum pouch filled with each sample was connected with a CPPEG connector (product name, manufactured by HANACO MEDICAL Co., Ltd.), and then a gastric-feeding-tube (manufactured by Bird, attached to a bird wizard) was connected with the connector. The length of the tube was 13 cm. On the sample, 5 kg of a weight (manufactured by SARTORIUS K.K., with a diameter of 87 mm) was placed still at room temperature for 40 seconds for extrusion while supporting the weight by the hands so as to prevent slippage drop of the weight without applying excess pressure. Then, the mass of the content extruded was measured. The measurement was performed three times with respect to each sample and results thereof were averaged.

TABLE 16

| Evaluation item | Sample 1 | Sample 2 | Sample 3 | Sample 4 | Sample 5 |
| --- | --- | --- | --- | --- | --- |
| Viscosity (mPa · s) | 1530 | 2810 | 2960 | 5320 | 12240 |
| Sensory evaluation | ⊚ | ⊚ | ⊚ | ○ | Δ |
| Extrusion amount (g) | 65.7 | 63.0 | 62.5 | 45.4 | 12.1 |

Figure 3:
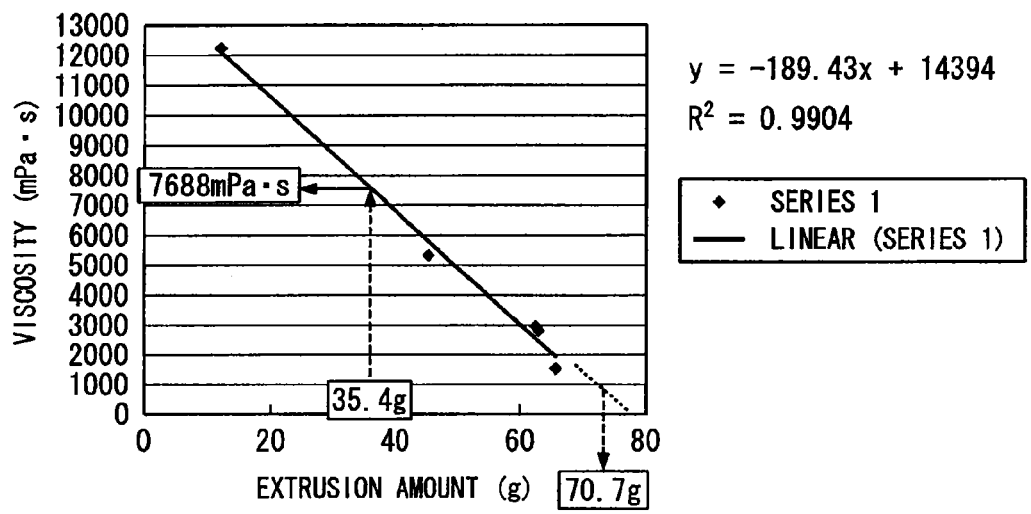
FIG. 3 is a graph showing the relationship between the viscosity of a composition and the extrusion properties thereof (Test Example 4).

The obtained results are shown in Table 16 and FIG. 3. As shown in Table 16, extrusion of the samples 1 to 4 was easily performed, however, extrusion of the sample 5 with a viscosity of over 10,000 mPa·s required pressure with a forearm strength that sensuously felt difficult in extrusion. Moreover, an approximated linear line was drawn by a method of least squares using a graph shown in FIG. 3, the graph illustrating relationship between the extrusion amount under constant pressure and the viscosity. The extrusion amount at a viscosity of 1,000 mPa·s, the amount being calculated using a numerical formula shown in the graph, was 70.7 g, and approximately half of the amount was considered to require a forearm strength within an allowable range for extrusion. The viscosity at the extrusion amount of 35.4 g, the viscosity being determined using a graph, was 7,688 mPa·s, and therefore at least a viscosity of 7,000 mPa·s or less was considered to contribute to obtaining a composition with a fluidity favorable in the practical use thereof. As is apparent from the results of the samples 1 to 3, the viscosity of 3,000 mPa·s or less realized extremely excellent fluidity, and allowed extremely easy use.

Test Example 5

Sample 6 prepared in Example 5 was subjected to a long-term stability test at room temperature (approximately at 25° C.) for six months. Physical properties of the sample 6 were measured at the start time of the test, and after the sample was left still for one, two, four, and six months at room temperature (approximately at 25° C.).

Particle Size Distribution

The particle size distribution was determined using a laser-scattering type device for measuring particle size (LS 13 320 (product name), manufactured by Beckman Coulter, Inc.) with a PIDS (polarization intensity differential scattering) assembly under conditions in which the refractive index of a liquid (suspension part) was 1.32, that of a sample, real part, was 1.45, and that of an imaginary part was 0.

Viscosity

The viscosity was measured using a rotary viscometer (BH-80 (product name), manufactured by TOKI SANGYO CO., LTD.) with a rotor No. 3 at 12 rpm.

Color Difference 5 g of each sample was put into a cell for measurement and the color difference was measured using a spectroscopic colorimeter (SE-2000 (product name), manufactured by NIPPON DENSHOKU INDUSTRIES CO., LTD.).

Sensory Evaluation

Comparison was performed in terms of taste, flavor, and feeling on the tongue, using each sample immediately after preparation as each standard sample. In the case in which the sample favorably compared with the standard sample, the sample was evaluated as suitable.

External Appearance

In the case in which the sample exhibited no phenomenon which was not recognized at the start time of the storage, such as, for example, generation of cream in accordance with change in an emulsification state, formation of insoluble salts, or significant change in color tone, the sample was evaluated as none.

TABLE 17

| Test item | | Unit | Start time | One month | Two months | Four months | Six months |
|---|---|---|---|---|---|---|---|
| Particle size distribution | Average particle size | μm | 22.77 | 26.74 | 25.42 | 26.11 | 25.23 |
| | Median size | μm | 19.28 | 22.53 | 20.91 | 20.92 | 21.54 |
| | Mode diameter | μm | 27.42 | 28.70 | 28.70 | 28.70 | 28.70 |
| Viscosity (25° C.) | | mPa·s | 2760 | 2040 | 3245 | 2065 | 3050 |
| pH (25° C.) | | | 6.1 | 6.1 | 6.1 | 6.0 | 5.9 |
| Color difference | ΔE | | 75.33 | 76.29 | 77.04 | 77.46 | 78.21 |
| | ΔL | | 39.32 | 38.46 | 37.89 | 36.92 | 36.94 |
| | Δa | | 15.62 | 16.04 | 16.33 | 16.40 | 17.26 |
| | Δb | | 44.14 | 44.47 | 44.90 | 44.26 | 45.28 |
| Sensory evaluation | | | — | Suitable | Suitable | Suitable | Suitable |
| External appearance (cream) | | | None | None | None | None | None |

The obtained results are shown in Table 17. Storage for six months did not cause significant change in terms of all of the particle size distribution, viscosity, pH, and color difference, and allowed the results in terms of all of the test items to fall within a determined range. That is, the results of the long-term stability test revealed that the sample 6 was excellent in stability and maintained a sufficient stability as a product for at least six months.

Next, the stability of the sample 6 was further evaluated by performing an accelerated test. The sample 6 was left still at 40° C., and then physical properties thereof were measured at the start time of the accelerated test and one and two months after the start time by the above-mentioned method.

TABLE 18

| Test item | | unit | Start time | One month | Two months |
|---|---|---|---|---|---|
| Particle size distribution | Average particle size | μm | 22.77 | 28.75 | 24.73 |
| | Median size | μm | 19.28 | 25.60 | 20.68 |
| | Mode diameter | μm | 27.42 | 31.50 | 27.42 |
| Viscosity (25° C.) | | mPa·s | 2760 | 2970 | 2865 |
| pH (25° C.) | | | 6.1 | 5.9 | 5.9 |
| Color difference | ΔE | | 75.33 | 76.91 | 79.49 |
| | ΔL | | 39.32 | 37.38 | 33.65 |
| | Δa | | 15.62 | 16.82 | 17.68 |
| | Δb | | 44.14 | 43.78 | 42.66 |
| Sensory evaluation | | | — | Suitable | Suitable |
| External appearance (cream) | | | None | None | None |

The obtained results are shown in Table 18. As is apparent from the results of the accelerated test, storage for two months after the start time of the test did not cause significant change in terms of all of the particle size distribution, viscosity, pH, and color difference, and allowed the results in terms of all of the test items to fall within a determined range. That is, the results of the accelerated test revealed that the sample 6 was excellent in stability and maintained stability even if the sample was left under a high-temperature atmosphere for a short time.

Test Example 6

A test with respect to washing efficiencies was performed under the following conditions using the above-mentioned samples 1, 3, and 4 as samples and TERUMEAL SOFT, TERUMEAL SOFT M, and TERUMEAL PG SOFT (trademark, manufactured by TERUMO CORPORATION) as contrast samples.

A balloon tube-type gastrostomy catheter (microbasive balloon G tube (product name) manufactured by Boston Scientific Japan K.K., 24 Fr. (thickness)), of which the mass was previously measured, was connected to a CPPEG connector (product name, manufactured by HANACO MEDICAL Co., Ltd.). Alternatively, a balloon bouton-type gastrostomy catheter (bird wizard (product name), manufactured by Bird, 24 Fr.) was connected to a PPEG connector (product name, manufactured by HANACO MEDICAL Co., Ltd.). Then, a gastric-feeding-tube with a length of 13 cm (manufactured by Bird, attached to a bird wizard) was connected with the CPPEG connector. Approximately 10 g of each sample or contrast sample was passed through, and then 15 ml of water was injected from a medical fluid port part of the catheter using a syringe to perform washing. After washing, the mass of each catheter was measured, and then the difference in the mass of the catheter was calculated between before and after passing the sample therethrough and then washing as the amount of the residual liquid by subtracting the mass of the catheter before passing the sample therethrough from the mass of the catheter after washing. In the case of the balloon bouton-type gastrostomy catheter, the amount of the residual liquid in both the catheter and the feeding tube was calculated. The above-mentioned test was performed five times, respectively, and then the average thereof was calculated. Also, the wall-surface of the tube was visually observed and evaluated in accordance with the following criteria.

○: Almost no sample was adhered to the wall-surface of the tube.

Δ: A slight amount of the sample was adhered to the wall-surface of the tube.

x: A significant amount of the sample was adhered to the wall-surface of the tube.

TABLE 19

| Sample name | Average (g) | Results of visual observation |
|---|---|---|
| TERUMEAL SOFT M | 1.100 | X |
| TERUMEAL SOFT | 0.922 | Δ |
| TERUMEAL PG SOFT | 0.892 | Δ |
| Sample 4 | 0.532 | ○ |
| Sample 3 | 0.424 | ○ |
| Sample 1 | 0.284 | ○ |

TABLE 20

| Sample name | Average (g) | Results of visual observation |
|---|---|---|
| TERUMEAL SOFT | 0.888 | Δ |
| Sample 3 | 0.466 | ○ |
| Sample 1 | 0.442 | ○ |

Figure 4:
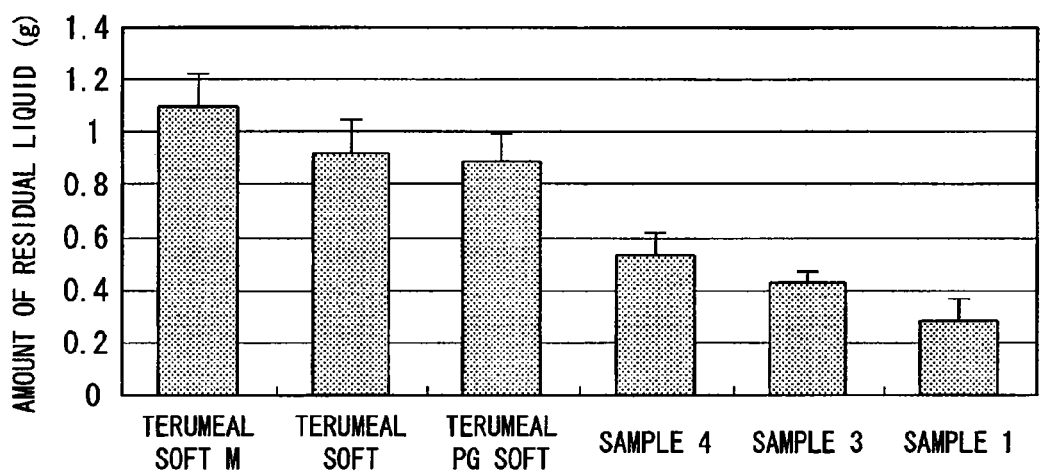
FIG. 4 is a graph showing each amount of residual liquid in a tube-type gastrostomy catheter washed after each composition is passed therethrough (Test Example 6).
Figure 5:
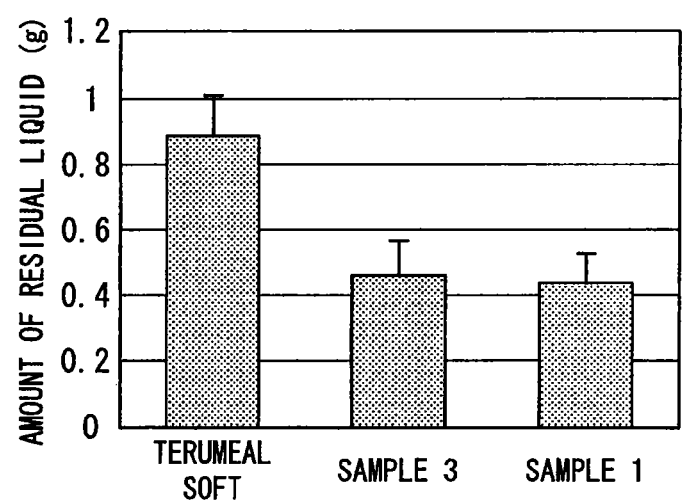
FIG. 5 is a graph showing each amount of residual liquid in a bouton-type gastrostomy catheter washed after each composition is passed therethrough (Test Example 6).

Each average of the amount of the residual liquid in the case of the tube-type gastrostomy catheter is shown in Table 19 and FIG. 4, and each average of the amount of the residual liquid in the case of the bouton-type gastrostomy catheter is shown in Table 20 and FIG. 5.

The results shown in Tables 19 and 20 and FIGS. 4 and 5 demonstrated that the samples 1, 3, and 4 exhibited significantly excellent washing efficiencies in comparison with the contrast samples.

INDUSTRIAL APPLICABILITY

According to the present invention, a nutrient composition containing a high protein content and other necessary nutrients in suitable quantities, the composition being able to be administered to patients by various administration methods easily, being excellent in heat-resistance for sterilization and storage-stability, and being able to be massively prepared at low cost without requiring any complicated manufacturing machines and steps, is provided. In particular, even if the formulation amount of protein or mineral was increased, a nutrient composition having rheologic properties favorable from the standpoint of oral intake or tubal administration is provided. In more detail, a nutrient composition containing sufficient amounts of protein and minerals, of which the conventional formulation amount in a nutrient composition with a high-calorie of over 1.5 kcal/ml is insufficient in the case where an energy intake is 1,000 kcal/day, the composition causing no problems in terms of production, distribution, and usage, is provided. Such a nutrient composition according to the present invention can be used in the field of foods for medical use.

What is claimed is:

1. A method of producing a nutrient composition, comprising:

the nutrient composition is prepared, in order:
adding a carbohydrate to water heated at 60° C. or more to make a heated solution;
adding a salt containing a monovalent cation to the heated solution;
then, adding a lipid, including: fats and oils;
adding a protein and stirring the heated solution with the lipids, to disperse and dissolve the protein, so that oil droplets are made to assemble and agglomerate by including the oil droplets in insolubilized protein particles; and
finally, adding a mineral including a salt comprising: a divalent cation therewith,
wherein a viscosity of the nutrient composition at 25° C. is 400 to 7,000 mPa's.

2. The method of producing the nutrient composition according to claim 1, further comprising adding an emulsifier to the nutrient composition.

3. The method of producing the nutrient composition according to claim 1, wherein the nutrient composition further comprises vitamins, fiber, and flavors.

4. The method of producing the nutrient composition according to claim 1, wherein a mass of the protein with respect to total moles of divalent cations forming water-insoluble particles is 1.5 to 3 g/mmol.

5. The method of producing the nutrient composition according to claim 1, wherein the divalent cation is selected from the group consisting citrate, sulphate, phosphate, carbonate, lactate, and hydrochloride.

6. The method of producing the nutrient composition according to claim 1, wherein stirring the heated solution comprises stirring at 5000 rpm or less.

* * * * *